(12) United States Patent
Flanagan et al.

(10) Patent No.: US 7,301,023 B2
(45) Date of Patent: Nov. 27, 2007

(54) CHIRAL SALT RESOLUTION

(75) Inventors: Mark E. Flanagan, Gales Ferry, CT (US); Michael J. Munchhof, Salem, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/154,699

(22) Filed: May 23, 2002

(65) Prior Publication Data
US 2003/0073719 A1 Apr. 17, 2003

Related U.S. Application Data

(60) Provisional application No. 60/341,048, filed on Dec. 6, 2001, and provisional application No. 60/294,775, filed on May 31, 2001.

(51) Int. Cl.
| C07D 487/04 | (2006.01) |
|---|---|
| C07D 213/74 | (2006.01) |
| A61K 31/519 | (2006.01) |
| A61P 35/00 | (2006.01) |
| C07B 57/00 | (2006.01) |

(52) U.S. Cl. .......................... 544/280; 546/22; 546/223
(58) Field of Classification Search ................ 544/280, 544/514, 265.1
See application file for complete search history.

(56) References Cited

U.S. PATENT DOCUMENTS

| 4,814,477 | A | 3/1989 | Wijnberg et al. | |
|---|---|---|---|---|
| 5,389,509 | A | 2/1995 | Maskasky | |
| 5,686,457 | A | 11/1997 | Traxler et al. | |
| 6,080,747 | A | 6/2000 | Uckun et al. | |
| 6,136,595 | A | 10/2000 | Ihle et al. | |
| 6,180,636 | B1 | 1/2001 | Traxler et al. | |
| 6,187,552 | B1 | 2/2001 | Roberds et al. | |
| 6,610,847 | B2 * | 8/2003 | Blumenkopf et al. | 544/280 |
| 6,635,762 | B1 * | 10/2003 | Blumenkopf et al. | 544/280 |
| 6,696,567 | B2 * | 2/2004 | Blumenkopf et al. | 544/280 |
| 6,965,027 | B2 * | 11/2005 | Flanagan et al. | 544/280 |
| 2001/0053782 | A1 * | 12/2001 | Blumenkopf et al. | 514/258 |
| 2002/0019526 | A1 * | 2/2002 | Blumenkopf et al. | 544/280 |
| 2002/0068746 | A1 * | 6/2002 | Blumenkopf et al. | 514/265.1 |

FOREIGN PATENT DOCUMENTS

| EP | 0795556 | 9/1997 |
|---|---|---|
| EP | 0682027 | 10/1997 |
| WO | WO 9519774 | 7/1995 |
| WO | WO 9713771 | 10/1995 |
| WO | WO 9802437 | 7/1996 |
| WO | WO 9802438 | 7/1996 |
| WO | WO 9640142 | 12/1996 |
| WO | WO 9702262 | 1/1997 |
| WO | WO 9702266 | 1/1997 |
| WO | WO 9718212 | 5/1997 |
| WO | WO 9727199 | 7/1997 |
| WO | WO 9728161 | 8/1997 |
| WO | WO 9732879 | 9/1997 |
| WO | WO 9749706 | 12/1997 |
| WO | WO 9807726 | 2/1998 |
| WO | WO 9823613 | 6/1998 |
| WO | WO 9833798 | 8/1998 |
| WO | WO 9951599 | 10/1999 |
| WO | WO 9961428 | 12/1999 |
| WO | WO 9965908 | 12/1999 |
| WO | WO 9965909 | 12/1999 |
| WO | WO 0000202 | 1/2000 |
| WO | WO 0010981 | 3/2000 |
| WO | WO 0142246 | 6/2001 |
| WO | WO 0200661 | 1/2002 |
| WO | WO 0348162 | 6/2003 |

OTHER PUBLICATIONS

"Advanced Organic Chemistry: Reactions, Mechanisms and Structure" 4th ed., (Jerry March, Wiley and Sons, 1992) p. 641–644.*
J. J. O'Shea, et al., *Phosphorylation and activation of the Jak–3 Janus Kinase in response to Interleukin–2*, Nature, 370, 151 (1994).
S. M. Russell, et al., *Interaction of IL–2Rβand γc Chains with Jak1 and Jak3: Implications for XSCID and XCID*, Science, 266, 1042 (1994).
J. N. Ihle, *The Janus Protein Tyrosine Kinase Family and Its Role in Cytokine Signaling*, Adv. Immunology, 60, 1, (1995).
J. N. Ihle, *The Janus Protein Tyrosine Kinases in hematopoietic cytokine signaling*, Semin. Immunology, 7, 247, (1995).
T. Musso, et al., *Regulation of JAK3 Expression in Human Monocytes: Phosphorylation in Response to Interleukings 2, 4, and 7*, J. Exp. Med., 181, 1425 (1995).
R. A. Kirken, et al., *Activation of JAK3, but not JAK1, is critical for IL–2–induced proliferation and STAT5 Recruitment by a COOH–terminal region of the IL–2–receptor β–chain*, Cytokine, 7 689, (1995).

(Continued)

*Primary Examiner*—Mark L. Berch
(74) *Attorney, Agent, or Firm*—Peter C. Richardson; Gregg C. Benson; Christine S. Lee

(57) ABSTRACT

A method for resolving enantiomers of a compound containing the structure of the forula:

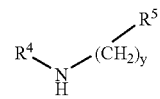

wherein $R^4$ or $R^5$ may contan one or more asymmetric centers, by mixing a racemic mixture of enantiomers of a compound, containing the structure of said formula; in a solvent, with a resolving compound having a defined sterospecificity, to form a solution and with said resolving agent being capable of binding with at least one but not all of said enantiomers to form a precipitate, containing said at least one of said enantiomers in sterospecific form and collecting either the precipitate and purifying it or collecting the solution with contained other of said enantiomers and recrystallizing the enantiomer contained in said solution.

1 Claim, No Drawings

OTHER PUBLICATIONS

M. G. Malabarba, et al., *Activation of JAK3, but not JAK1, is Critical to Interleukin–4 (IL4) Stimulated Proliferation and Requires a Membrane–proximal Region of IL4 Receptor α*, J. Biol. Chem., 270, 9630, (1995).

J. H. Hanke, B. A. Pollok, and P. S. Changelian, *Role of tyrosine kinases in lymphocyte activation: Targets for drug intervention.* Inflamm. Res., 44, 357, (1995).

E. E. Eynon, et al., *Disruption of Cytokine Signaling in Lymphoid Development: Unique Contributions of the Common Cytokine Gamma Chain and the JAK3 Kinase*, J. Interferon Cytokine Res., 16, 677, (1996).

S. A. Oakes, et al., *Signaling via IL–2 and IL–4 in JAK#–Deficient Severe Combined Immunodeficiency Lymphocytes: JAK3–Dependent and Independent Pathways*, Immunity, 5, 605 (1996).

L. D. Norangelo, et al, *Severe Combined Immune Deficiency due to Defects of the JAK3 Tyrosine Kinase*, Prog. Immunodeficiency, 6, 61, (1996).

D. C. Thomis, et al., *Peripheral Expression of JAK3 is Required to Maintain T Lymphocyte Function*, J. Exp. Med., 185, 197, (1997).

B. H. Nelson, et al., *Requirement for an initial signal from the membrane–proximal region of the interleukin 2 receptor γc chain for Janus kinase activation leading to T cell proliferation*, Proc. Natl. Acad. Sci. USA, 94, 1878, (1997).

A. M. Baird, et al., *T Cell development and activation in Jak3–deficient mice*, J. Leukocyte Biol., 63, 669, (1998).

K. D. Liu, et al., *JAK/STAT signaling by cytokine receptors*, Curr. Opin. Immunol., 1998, 10:271–278.

W. J. Leonard and J. J. O'Shea, *JAKS and STATS: Biological Implications*, Annu. Rev. Immunol., 16, 293, (1998).

F. Candotti, et al., *Severe combined immune deficiencies due to defects in the common γ chain–JAK3 signaling pathway*, Springer Semin. Immuopathol., 19, 401, (1998).

R. Malaviya, et al., *Targeting Janus Kinase 3 in Mast Cells Prevents Immediate Hypersensitivity Reactions and Anaphylaxis*, J. Biol. Chem., 274, 27028 (1999).

D. C. Thomis, et al., *The Jak Family Tyrosine Kinase Jak3 is Required for IL–2 Synthesis by Naive/Resting CD4+ T Cells*, J. Immunol., 163, 5411 (1999).

E. Chen, et al., *Advances in Cytokine Signaling: The Role of Jaks and STATs*, Transplantation Proc., 31, 1482, (1999).

R. Moriggi, et al., *Stat5 Activation is Uniquely Associated with Cytokine Signaling in Peripheral T Cells*, Immunity, 11, 225 (1995).

L. H. Wang, et al., *JAK3, STAT, and MAPK Signaling Pathways as Novel Molecular Targets for the Tyrphostin AG–490 Regulation of IL–2–Mediated T Cell Response*, J. Immunol., 162, 3897, (1999).

E. A. Sudbeck, et al., *Structure–based Design of Specific Inhibitors of Janus Kinase 3 as Apoptosis–inducing Antileukemic Agents*, Clin. Cancer Res., 5, 1569, (1999).

F. M. Uckun, et al., *In Vivo Toxicity and Pharmacokinetic Features of the Janus Kinase 3 Inhibitor WHI–P131 [40(4'–Hydroxyphenyl)–Amino–6, 7–Dimethosyquinazoline]*, Clin. Cancer Research, 5, 2954, (1999).

E. A. Sudbeck and F. M. Uckun, *Recent Advances in JAK3 kinase inhibitors*, IDrugs, 2, 1026, (1999).

R. Malaviya, et al., *Genetic and Biochemical Evidence for a Critical Role of Janus Kinase (JAK)–3 in Mast Cell–Mediated Type I Hypersenstivity Reactions*, Biochem. Biophys., Res. Commun., 257, 807, (1999).

V. N. Trieu, et al., *A Specific Inhibitor of Janus Kinase–3 Increases Survival in a Transgenic Mouse Model of Amyotrophic Lateral Sclerosis*, Biochem. Biophys. Res. Commun., 267, 22, (2000).

X. C. Li, et. al., *Blocking the Common γ–Chain of Cytokine Receptors Induces T Cell Apoptosis and Long–Term Islet Allograft Survival*, J. Immunol., 164, 1193 (2000).

R. Malaviya, et al., *Treatment of allergic asthma by targeting Janus kinase 3–dependent leukotriene synthesis in mast cells with 4–(3', 5'–Dibromo–4 'hydroxphenyl)amino–6, 7–dimethoxyquinazoline(WHI–P97)*, J. Pharmacol. Exp. Ther., 295, 912 (2000).

Traxler, P. M., et al., *Protein tyrosine kinase inhibitors in cancer treatment*, Exp. Opin. Ther. Patents. (1997), 7 (6): 571–588.

Traxler, P. M., et al., *4–(phenylamino)pyrrolopyrimidine: Potent and Selective, ATP Site Directed Inhibitors of the EGF–Receptor Protein Tyrosine Kinase*, J. Med. Chem., (1996), 39, 2285–2292.

Jacques, Jean, *Enantiomers, racemates, and resolutions*, J. Riley & Sons, Inc. XP002208813, (1981) 251–273.

Bayley, C.R., et al. *Resolution of Racemates by Diastereomeric Salt Formation*, J. Riley & Sones, England, XP002208814, (1992)69–77, in *Chirality in industry: the commercial manufacture and applications of optically active compounds*.

Patent Abstracts of Japan, vol. 1996, No. 4, Apr. 30, 1996 and JP 07330732 A (Kyorin Pharmaceut Co., LTD) Dec. 19, 1995.

\* cited by examiner

CHIRAL SALT RESOLUTION

CROSS-REFERENCE TO RELATED APPLICATION

This non-provisional application claims priority from U.S. provisional application No. 60/294,775, filed May 31, 2001, and U.S. provisional application No. 60/341,048, filed Dec. 6, 2001.

FIELD OF THE INVENTION

The present invention relates to methods for effecting chiral salt resolution from racemic mixtures of enantiomers and particularly precursor enantiomers used in making pyrrolo[2,3-d]pyrimidine compounds, which are inhibitors of protein kinases. The present invention also relates to pyrrolyl[2,3-d]pyrimidine compounds and methods of using such compounds as inhibitors of protein kinases, such as the enzyme Janus Kinase 3.

BACKGROUND OF THE INVENTION

Pyrrolo[2,3-d]pyrimidine compounds are inhibitors of protein kinases, such as the enzyme Janus Kinase 3 (JAK3) and are therefore useful therapy as immunosuppressive agents for organ transplants, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable. The pyrrolo[2,3-d]pyrimidine compounds, pharmaceutical compositions thereof and methods of use are described in co-pending application Ser. No. 09/732669, filed Dec. 8, 2000, and assigned to the assignee of the present invention. The disclosure of said application is included in its entirety herein by reference thereto. Racemic mixtures of the pyrrolo [2,3-d]pyrimidine compounds are initially obtained whereas the individual enantiomers in substantially isolated pure form are preferred and at times required for drug use. It is possible to pre-ordain the stereochemistry of the compounds by use of stereospecific precursor compounds in the sythesis thereof. The methods of the present invention accordingly specifically relate to a method for the substantial chiral salt resolution of racemic mixtures of precursor compounds, used in the production of the separate enantiomeric forms of the pyrrolo[2,3-d]pyrimidine compounds.

SUMMARY OF THE INVENTION

The present invention relates to methods for resolving the enantiomers of the precursors used in preparing a compound of the following formula and particularly the $R^1$ group thereof:

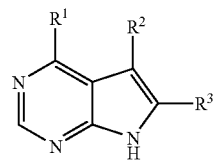

I or the pharmaceutically acceptable salt thereof; wherein $R^1$ is a group of the formula

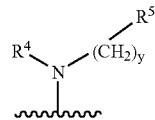

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$ amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$ alkylamino, $((C_1-C_6)$alkyl$)_2$amino, cyano, cyano $(C_1-C_6)$alkyl, trifluoromethyl$(C_1-C_6)$alkyl, nitro, nitro $(C_1-C_6)$alkyl or $(C_1-C_6)$acylamino;

$R^5$ is $(C_1-C_9)$heterocycloalkyl wherein the heterocycloalkyl groups must be substituted by one to five carboxy, cyano, amino, deuterium, hydroxy, $(C_1-C_6)$ alkyl, $(C_1-C_6)$alkoxy, halo, $(C_1-C_6)$acyl, $(C_1-C_6)$ alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, amino$(C_1-C_6)$ alkyl, hydroxy$(C_1-C_6)$alkyl, $(C_1-C_6)$alkoxy$(C_1-C_6)$ alkyl, $(C_1-C_6)$acyloxy$(C_1-C_6)$alkyl, nitro, cyano $(C_1-C_6)$alkyl, halo$(C_1-C_6)$alkyl, nitro$(C_1-C_6)$alkyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy $(C_1-C_6)$acylamino, amino$(C_1-C_6)$acyl, amino$(C_1-C_6)$ acyl$(C_1-C_6)$alkyl, $(C_1-C_6)$alkylamino$(C_1-C_6)$acyl, $((C_1-C_6)$alkyl$)_2$amino$(C_1-C_8)$acyl, $R^{15}R^{16}N$—CO—O—, $R^{15}R^{16}N$—CO—$(C_1-C_6)$alkyl, $(C_1-C_6)$alkyl-S$(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula II:

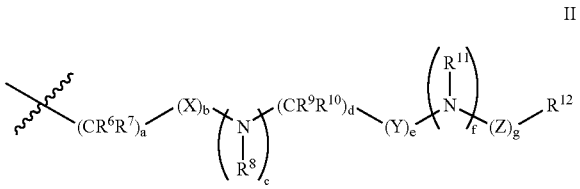

II wherein a is 0, 1, 2, 3 or 4;

b, c, e, f and g are each independently 0 or 1;

d is 0, 1, 2, or 3;

X is $S(O)_n$ wherein n is 0, 1 or 2; oxygen, carbonyl or —C(=N-cyano)-;

Y is $S(O)_n$ wherein n is 0, 1 or 2; or carbonyl; and

Z is carbonyl, C(O)O—, C(O)NR— or $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, ($C_1$–$C_6$)acylamino, ($C_1$–$C_6$)alkylamino, (($C_1$–$C_6$)alkyl)$_2$amino, cyano, cyano($C_1$–$C_6$)alkyl, trifluoromethyl($C_1$–$C_6$)alkyl, nitro, nitro($C_1$–$C_6$)alkyl or ($C_1$–$C_6$)acylamino;

$R^{12}$ is carboxy, cyano, amino, oxo, deuterium, hydroxy, trifluoromethyl, ($C_1$–$C_6$)alkyl, trifluoromethyl($C_1$–$C_6$)alkyl, ($C_1$–$C_6$)alkoxy, halo, ($C_1$–$C_6$)acyl, ($C_1$–$C_6$)alkylamino, (($C_1$–$C_6$)alkyl)$_2$ amino, amino($C_1$–$C_6$)alkyl, ($C_1$–$C_6$)alkoxy-CO—NH, ($C_1$–$C_6$)alkylamino-CO—($C_2$–$C_6$)alkenyl, ($C_2$–$C_6$) alkynyl, ($C_1$–$C_6$) alkylamino, hydroxy($C_1$–$C_6$)alkyl, ($C_1$–$C_6$)alkoxy ($C_1$–$C_6$)alkyl, ($C_1$–$C_6$)acyloxy($C_1$–$C_6$)alkyl, nitro, cyano($C_1$–$C_6$)alkyl, halo($C_1$–$C_6$)alkyl, nitro($C_1$–$C_6$)alkyl, trifluoromethyl, trifluoromethyl($C_1$–$C_6$)alkyl, ($C_1$–$C_6$)acylamino, ($C_1$–$C_6$)acylamino($C_1$–$C_6$)alkyl, ($C_1$–$C_6$)alkoxy($C_1$–$C_6$)acylamino, amino($C_1$–$C_6$)acyl, amino($C_1$–$C_6$)acyl($C_1$–$C_6$)alkyl, ($C_1$–$C_6$)alkylamino ($C_1$–$C_6$)acyl, (($C_1$–$C_6$)alkyl)$_2$amino($C_1$–$C_6$)acyl, $R^{15}R^{16}$N—CO—O—, $R^{15}R^{16}$N—CO—($C_1$–$C_6$)alkyl, $R^{15}$C(O)NH, $R^{15}$OC(O)NH, $R^{15}$NHC(O)NH, ($C_1$–$C_6$)alkyl-S(O)$_m$, ($C_1$–$C_6$)alkyl-S(O)$_m$—($C_1$–$C_6$)alkyl, $R^{15}R^{16}$NS(O)$_m$, $R^{15}R^{16}$NS(O)$_m$($C_1$–$C_6$)alkyl, $R^{15}$S(O)$_m$ $R^{16}$N, $R^{15}$S(O)$_m$$R^{16}$N($C_1$–$C_6$)alkyl wherein m is 0, 1 or 2 and $R^{15}$ and $R^{16}$ are each independently selected from hydrogen or ($C_1$–$C_6$)alkyl;

$R^2$ and $R^3$ are each independently selected from the group consisting of hydrogen, deuterium, amino, halo, hydoxy, nitro, carboxy, ($C_2$–$C_6$)alkenyl, ($C_2$–$C_6$)alkynyl, trifluoromethyl, trifluoromethoxy, ($C_1$–$C_6$)alkyl, ($C_1$–$C_6$)alkoxy, ($C_3$–$C_{10}$)cycloalkyl wherein the alkyl, alkoxy or cycloalkyl groups are optionally substittued by one to three groups selected from halo, hydroxy, carboxy, amino ($C_1$–$C_6$)alkylthio, ($C_1$–$C_6$)alkylamino, (($C_1$–$C_6$)alkyl)$_2$amino, ($C_5$–$C_9$)heteroaryl, ($C_2$–$C_9$)heterocycloalkyl, ($C_3$–$C_9$)cycloalkyl or ($C_6$–$C_{10}$)aryl; or $R^2$ and $R^3$ are each independently ($C_3$–$C_{10}$)cycloalkyl, ($C_3$–$C_{10}$)cycloalkoxy, ($C_1$–$C_6$)alkylamino, (($C_1$–$C_6$)alkyl)$_2$amino, ($C_6$–$C_{10}$)arylamino, ($C_1$–$C_6$)alkylthio, ($C_6$–$C_{10}$)arylthio, ($C_1$–$C_6$)alkylsulfinyl, ($C_6$–$C_{10}$)arylsulfinyl, ($C_1$–$C_6$)alkylsulfonyl, ($C_6$–$C_{10}$)arylsulfonyl, ($C_1$–$C_6$)acyl, ($C_1$–$C_6$)alkoxy-CO—NH—, ($C_1$–$C_6$)alkyamino-CO—, ($C_5$–$C_9$)heteroaryl, ($C_2$–$C_9$)heterocycloalkyl or ($C_6$–$C_{10}$)aryl wherein the heteroaryl, heterocycloalkyl and aryl groups are optionally substituted by one to three halo, ($C_1$–$C_6$)alkyl, ($C_1$–$C_6$)alkyl-CO—NH—, ($C_1$–$C_6$)alkoxy-CO—NH—, ($C_1$–$C_6$)alkyl-CO—NH—($C_1$–$C_6$)alkyl, ($C_1$–$C_6$)alkoxy-CO—NH—($C_1$–$C_6$)alkyl, ($C_1$–$C_6$)alkoxy-CO—NH—($C_1$–$C_6$)alkoxy, carboxy, carboxy($C_1$–$C_6$)alkyl, carboxy ($C_1$–$C_6$)alkoxy, benzyloxycarbonyl($C_1$–$C_6$)alkoxy, ($C_1$–$C_6$)alkoxycarbonyl($C_1$–$C_6$)alkoxy, ($C_6$–$C_{10}$)aryl, amino, amino($C_1$–$C_6$)alkyl, ($C_1$–$C_6$)alkoxycarbonylamino, ($C_6$–$C_{10}$)aryl($C_1$–$C_6$)alkoxycarbonylamino, ($C_1$–$C_6$)alkylamino, (($C_1$–$C_6$)alkyl)$_2$amino, ($C_1$–$C_6$)alkylamino($C_1$–$C_6$)alkyl, (($C_1$–$C_6$)alkyl)$_2$amino($C_1$–$C_6$)alkyl, hydroxy, ($C_1$–$C_6$)alkoxy, carboxy, carboxy($C_1$–$C_6$)alkyl, ($C_1$–$C_6$)alkoxycarbonyl, ($C_1$–$C_6$)alkoxycarbonyl($C_1$–$C_6$)alkyl, ($C_1$–$C_6$)alkoxy-CO—NH—, ($C_1$–$C_6$)alkyl-CO—NH—, cyano, ($C_5$–$C_9$)heterocycloalkyl, amino-CO—NH—, ($C_1$–$C_6$)alkylamino-CO—NH—, (($C_1$–$C_6$)alkyl)$_2$amino-CO—NH—, ($C_6$–$C_{10}$)arylamino-CO—NH—, ($C_5$–$C_9$)heteroarylamino-CO—NH—, ($C_1$–$C_6$)alkylamino-CO—NH—($C_1$–$C_6$)alkyl, (($C_1$–$C_6$)alkyl)$_2$amino-CO—NH—($C_1$–$C_6$)alkyl, $C_6$–$C_{10}$)arylamino-CO—NH—($C_1$–$C_6$)alkyl, ($C_5$–$C_9$)heteroarylamino-CO—NH—($C_1$–$C_6$)alkyl, ($C_1$–$C_6$)alkylsulfonyl, ($C_1$–$C_6$)alkylsulfonylamino, ($C_1$–$C_6$)alkylsulfonylamino($C_1$–$C_6$)alkyl, ($C_6$–$C_{10}$)arylsulfonyl, ($C_6$–$C_{10}$)arylsulfonylamino, ($C_6$–$C_{10}$)arylsulfonylamino($C_1$–$C_6$)alkyl, ($C_1$–$C_6$)alkylsulfonylamino, ($C_1$–$C_6$)alkylsulfonylamino ($C_1$–$C_6$)alkyl, ($C_5$–$C_9$)heteroaryl or ($C_2$–$C_9$)heterocycloalkyl.

The present invention also relates to the production of stereospecific pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to stereospecific base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "alkyl", as used herein, unless otherwise indicated, includes saturated monovalent hydrocarbon radicals having straight or branched moieties or combinations thereof.

The term "alkoxy", as used herein, includes O-alkyl groups wherein "alkyl" is defined above.

The term "halo", as used herein, unless otherwise indicated, includes fluoro, chloro, bromo or iodo. The compounds of this invention may contain double bonds. When such bonds are present, the compounds of the invention exist as cis and trans configurations and as mixtures thereof. Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

($C_2$–$C_9$)Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said ($C_2$–$C_9$)heterocycloalkyl rings is through a carbon or a sp$^3$ hybridized nitrogen heteroatom.

($C_2$–$C_9$)Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3,-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1] pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said ($C_2$–$C_9$) heterocycloalkyl rings is through a carbon atom or a $sp^3$ hybridized nitrogen heteroatom.

($C_6$–$C_{10}$)aryl when used herein refers to phenyl or naphthyl.

The compounds used in this invention include all conformational isomers (e.g., cis and trans isomers. The compounds used in present invention have asymmetric centers and are therefore chiral and exist in different enantiomeric and diastereomeric forms. This invention relates to the resolution of optical isomers and stereoisomers of the precursors of constituents and thereby compounds of the present invention, and mixtures thereof, and to all pharmaceutical compositions and methods of treatment that may employ or contain them. In this regard, the invention includes both the E and Z configurations. The compounds of formula I may also exist as tautomers. This invention relates to such tautomers and mixtures thereof. In particular, resolution of racemic mixtures of enantiomers of compounds, used in providing the $R^1$ substituent of formula I, is effected by treating the racemic mixture with a specific optical isomer of a disubstituted tartaric acid or tartrate in an appropriate solvent such as ethanol with or without water as a co-solvent. Resolution in obtaining the desired enantiomer in excess of 90% is possible in accordance with the method of the present invention with the use of resolving agents such as the optical isomers of tartaric acid and tartaric acid derivatives such as di-p-toluoyl-L-tartaric acid and (S)-(+)-Andeno acid (pencyphos, (S)-(+)-2-hydroxy-5,5-dimethyl-4-phenyl-1,3,2-dioxyphosphorinane-2-oxide) salt.

Interaction between antipodes of the resolving material and specific enantiomer provides a resolution of the racemic mixture whereby a precipitate of the resolving material and enantiomer provides one of the desired stereospecific materials and wherein the remaining enantiometer in solution can be separately isolated thereby. Thus, depending on the specific enantiomer desired and the separation method to be used (i.e., from precipitate or solution), the stereospecific nature of the resolving nature can be concomitantly selected; e.g. an "L" form of the resolving agent such as a tartrate derivative provides a precipitate of an "R" form of the $R^1$ substituent and a solution containing the "L" form and vice versa.

The aforementioned resolving agents are effective in providing a 3R,4R enantiomer of the compound of the formula (either in precipitate or solution, as described):

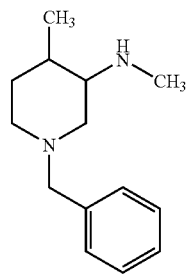

In accordance with the present invention the method of resolution of the compound of formula III is effected by the steps of:
  a) mixing a racemic mixture of the compound of formula III in an appropriate solution with a resolving compound, having a defined stereospecificity, for a time sufficient to allow substantial precipitation of a stereospecific isomer of the racemic mixture from the solution;
  b) depending on the stereospecific form of the compound which is desired, collecting either the precipitate and purifying it or collecting the mother liquor and recrystallizing the enantiomer contained therein.

With some materials a slurry rather that a solution is formed with the resolution of the present invention involving a slurry to slurry conversion. The term "solution" encompasses both a solution and a slurry.

The temperature at which the resolution and precipitation is effected is preferably ambient temperature and while precipitation time is not restricted for efficicency the time is preferably no more than about four hours. In order to facilitate the resolution it is desirable to use enantiomers in the racemic mixture which are in a stable form and the compound of formula II is most stable in acid addition salt form such as a hydrochloride salt, rather than a free base form and it is preferred that the racemic compound mixture be accordingly converted prior to resolution. Thus, for example, formation of the hydrochloride salt of the compound of formula II is effected preferably in ethanol with a small amount of toluene as cosolvent. Alternatively, methanol, isopropanol, acetonitrile, or tetrahydrofuran (or mixtures thereof with or without water as a cosolvent) with cosolvents of toluene, ethylacetate, dichloromethane, dichloroethane, or tetrahydrofuran may be used in the salt formation. The HCl salt is particularly preferred since this form provides a superior purification and enriched of other stereomers from the prior step.

A preferred displacement solvent to be used in the resolution is ethyl acetate. Toluene, acetonitrile, or heptanes are also useful as solvents.

A preferred isolation solvent is acetone. Other solvents useful in this regard include isopropanol, ethanol, methyl ethyl ketone, methyl isopropyl ketone, acetonitrile, and tetrahydrofuran. The solvents may also be used as co-solvents with each other or with water.

Preferred resolution compounds include tartaric acid and its derivatives such as toluoyl and benzoyl tartaric acids in stereospecific conformation, as described. Other resolution compounds include sperespecific adeno acid and derivatives thereof.

To facilitate precipitation and recrystalization addition of seeds is optional, but preferred in order to obtain higher ee material with fewer recrystalizations.

In order to illustrate the procedure and efficacy of the present invention the following examples are presented. It is understood that such examples are details contained therein are not to be construed as limitations on the present invention.

The present invention also relates to a method for preparing the compound of the formula:

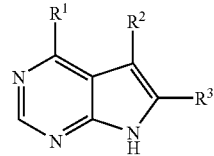

I or the pharmaceutically acceptable salt thereof; wherein $R^1$ is a group of the formula

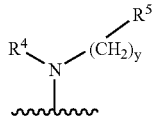

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano $(C_1-C_6)$alkyl, trifluoromethyl$(C_1-C_6)$alkyl, nitro, nitro $(C_1-C_6)$alkyl or $(C_1-C_6)$acylamino;

$R^5$ is $(C_1-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$ alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano $(C_1-C_6)$alkyl, halo$(C_1-C_6)$alkyl, nitro$(C_1-C_6)$alkyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy $(C_1-C_6)$acylamino, amino$(C_1-C_6)$acyl, amino$(C_1-C_6)$ acyl$(C_1-C_6)$alkyl, $(C_1-C_6)$alkylamino$(C_1-C_6)$acyl, $((C_1-C_6)$alkyl$)_2$amino$(C_1-C_8)$acyl, $R^{15}R^{16}N$—CO—O—, $R^{15}R^{16}N$—CO—$(C_1-C_6)$alkyl, $(C_1-C_6)$alkyl-S$(O)_m$, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula II:

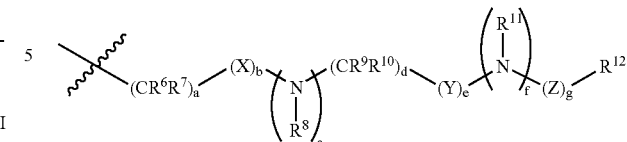

II wherein a is 0, 1, 2, 3 or 4;

b, c, e, f and g are each independently 0 or 1;

d is 0, 1, 2, or 3;

X is $S(O)_n$ wherein n is 0, 1 or 2; oxygen, carbonyl or —C(=N-cyano)-;

Y is $S(O)_n$ wherein n is 0, 1 or 2; or carbonyl; and

Z is carbonyl, C(O)O—, C(O)NR— or $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$ alkyl, $(C_1-C_6)$alkoxy, halo, $(C_1-C_6)$acyl, $(C_1-C_6)$ alkylamino, $((C_1-C_6)$alkyl$)_2$ amino, amino$(C_1-C_6)$ alkyl, $(C_1-C_6)$alkoxy-CO—NH, $(C_1-C_6)$alkylamino-CO—$(C_2-C_6)$alkenyl, $(C_2-C_6)$ alkynyl, $(C_1-C_6)$ alkylamino, hydroxy$(C_1-C_6)$alkyl, $(C_1-C_6)$alkoxy $(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$ alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino $(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$ alkyl-S$(O)_m$, $(C_1-C_6)$alkyl-S$(O)_m$—$(C_1-C_6)$alkyl, $R^{15}R^{16}NS(O)_m$, $R^{15}R^{16}NS(O)_m(C_1-C_6)$alkyl, $R^{15}S(O)_m R^{16}N$, $R^{15}S(O)_m R^{16}N(C_1-C_6)$alkyl wherein m is 0, 1 or 2 and $R^{15}$ and $R^{16}$ are each independently selected from hydrogen or $(C_1-C_6)$alkyl;

$R^2$ and $R^3$ are each independently selected from the group consisting of hydrogen, deuterium, amino, halo, hydoxy, nitro, carboxy, $(C_2-C_6)$alkenyl, $(C_2-C_6)$ alkynyl, trifluoromethyl, trifluoromethoxy, $(C_1-C_6)$ alkyl, $(C_1-C_6)$alkoxy, $(C_3-C_{10})$cycloalkyl wherein the alkyl, alkoxy or cycloalkyl groups are optionally substittued by one to three groups selected from halo, hydroxy, carboxy, amino $(C_1-C_6)$alkylthio, $(C_1-C_6)$ alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$ alkylamino, $((C_1-C_6)$alkyl$)_2$amino, $(C_6-C_{10})$ arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$ alkylsulfonyl, $(C_6-C_{10})$arylsulfonyl, $(C_1-C_6)$acyl, $(C_1-C_6)$alkoxy-C)—NH—, $(C_1-C_6)$alkyamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$amino, $(C_1-C_6)$alkylamino$(C_1-C_6)$alkyl, $((C_1-C_6)$alkyl$)_2$amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$amino-CO—NH—$(C_1-C_6)$alkyl, $(C_6-C_{10})$arylamino-CO—NH—$(C_1-C_6)$alkyl, $(C_5-C_9)$heteroarylamino-CO—NH—$(C_1-C_6)$alkyl, $(C_1-C_6)$alkylsulfonyl, $(C_1-C_6)$alkylsulfonylamino, $(C_1-C_6)$alkylsulfonylamino$(C_1-C_6)$alkyl, $(C_6-C_{10})$arylsulfonyl, $(C_6-C_{10})$arylsulfonylamino, $(C_6-C_{10})$arylsulfonylamino$(C_1-C_6)$alkyl, $(C_1-C_6)$alkylsulfonylamino, $(C_1-C_6)$alkylsulfonylamino$(C_1-C_6)$alkyl, $(C_5-C_9)$heteroaryl or $(C_2-C_9)$heterocycloalkyl;

said method comprising the steps of:

a) mixing a racemic mixture of enantiomeric compounds of the formula

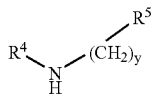

wherein y, $R^4$ and $R^5$ are as defined above, in a solvent, with a resolving compound having a defined stereospecificity, to form a solution and with said resolving agent being capable of binding with at least one but not all of said enantiomers to form a precipitate, containing said at least one of said enantiomers, b) allowing the mixture to stand for a time sufficient to allow substantial precipitation of a stereospecific enantiomer of the racemic mixture from the solution and wherein another of said enantiomers remains in said solution;

c) depending on the stereospecific enantiomer of the compound which is desired, collecting either the precipitate and purifying it or collecting the solution with contained other of said enantiomers and recrystallizing the enantiomer contained in said solution; and d) reacting the desired stereospecific enantiomer so formed with a compound of the formula

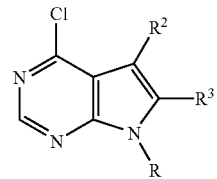

XVI wherein R is hydrogen or a protecting group and $R^2$ and $R^3$ are as defined above.

The present invention also relates to a compound of the formula

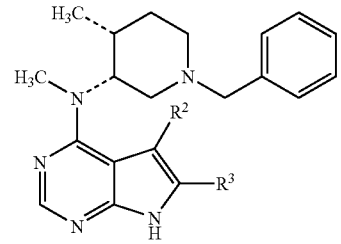

wherein $R^2$ and $R^3$ are each independently selected from the group consisting of hydrogen, deuterium, amino, halo, hydoxy, nitro, carboxy, $(C_2-C_6)$alkenyl, $(C_2-C_6)$alkynyl, trifluoromethyl, trifluoromethoxy, $(C_1-C_6)$alkyl, $(C_1-C_6)$alkoxy, $(C_3-C_{10})$cycloalkyl wherein the alkyl, alkoxy or cycloalkyl groups are optionally substituted by one to three groups selected from halo, hydroxy, carboxy, amino $(C_1-C_6)$alkylthio, $(C_1-C_6)$alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkyamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$amino, $(C_1-C_6)$alkylamino$(C_1-C_6)$alkyl, $((C_1-C_6)$alkyl$)_2$amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$ alkyl)$_2$amino-CO—NH—(C$_1$–C$_6$)alkyl, (C$_6$–C$_{10}$)arylamino-CO—NH—(C$_1$–C$_6$)alkyl, (C$_5$–C$_9$)heteroarylamino-CO—NH—(C$_1$–C$_6$)alkyl, (C$_1$–C$_6$)alkylsulfonyl, (C$_1$–C$_6$)alkylsulfonylamino, (C$_1$–C$_6$)alkylsulfonylamino(C$_1$–C$_6$)alkyl, (C$_6$–C$_{10}$)arylsulfonyl, (C$_6$–C$_{10}$)arylsulfonylamino, (C$_6$–C$_{10}$)arylsulfonylamino(C$_1$–C$_6$)alkyl, (C$_1$–C$_6$)alkylsulfonylamino, (C$_1$–C$_6$)alkylsulfonylamino(C$_1$–C$_6$)alkyl, (C$_5$–C$_9$)heteroaryl or (C$_2$–C$_9$)heterocycloalkyl.

The present invention also relates to specifically preferred compounds selected from the group consisting of:

Methyl-[(3R,4R)-4-methyl-1-(propane-1-sulfonyl)-piperidin-3-yl]-(7H-pyrrolo[2,3-d]pyrimidin-4-yl)-amine;

(3R,4R)-)-4-Methyl-3-[methyl-(7H-pyrrolo[2,3-d]pyrimidin4-yl)-amino]-piperidine-1-carboxylic acid methyl ester;

3,3,3-Trifluoro-1-{(3R,4R)-4-methyl-3-[methyl-(7H-pyrrolo[2,3-d]pyrimidin-4-yl)-amino]-piperidin-1-yl}-propan-1-one;

(3R,4R)-4-Methyl-3-[methyl-(7H-pyrrolo[2,3-d]pyrimidin-4-yl)-amino]-piperidine-1-carboxylic acid dimethylamide;

{(3R,4R)-4-Methyl-3-[methyl-(7H-pyrrolo[2,3-d]pyrimidin-4-yl)-amino]-piperidine-1-carbonyl}-amino)-acetic acid ethyl ester;

3-{(3R,4R)-4-Methyl-3-[methyl-(7H-pyrrolo[2,3-d]pyrimidin4-yl)-amino]-piperidin-1-yl}-3-oxo-propionitrile;

3,3,3-Trifluoro-1-{(3R,4R)-4-methyl-3-[methyl-(5-methyl-7H-pyrrolo[2,3-d]pyrimidin-4-yl)-amino]-piperidin-1-yl}-propan-1-one;

1-{(3R,4R)-4-Methyl-3-[methyl-(7H-pyrrolo[2,3-d]pyrimidin-4-yl)-amino]-piperidin-1-yl}-but-3-yn-1-one;

1-{(3R,4R)-3-[(5-Chloro-7H-pyrrolo[2,3-d]pyrimidin-4-yl)-methyl-amino]-4-methyl-piperidin-1-yl}-propan-1-one;

1-{(3R,4R)-3-[(5-Fluoro-7H-pyrrolo[2,3-d]pyrimidin-4-yl)-methyl-amino]-4-methyl-piperidin-1-yl}-propan-1-one;

(3R,4R)-N-cyano-4-methyl-3-[methyl-(7H-pyrrolo[2,3-d]pyrimidin-4-yl)-amino]-N'-propyl-piperidine-1-carboxamidine; and (3R,4R)-N-cyano-4,N',N'-Trimethyl-3-[methyl-(7H-pyrrolo[2,3-d]pyrimidin4-yl)-amino]-piperidine-1-carboxamidine.

The present invention also relates to a pharmaceutical composition for (a) treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases or (b) the inhibition of protein kinases or Janus Kinase 3 (JAK3) in a mammal, including a human, comprising an amount of an above described specifically preferred compound or a pharmaceutically acceptable salt thereof, effective in such disorders or conditions and a pharmaceutically acceptable carrier.

The present invention also relates to a method for the inhibition of protein tyrosine kinases or Janus Kinase 3 (JAK3) in a mammal, including a human, comprising administering to said mammal an effective amount of an above described specifically preferred compound or a pharmaceutically acceptable salt thereof.

The present invention also relates to a method for treating or preventing a disorder or condition selected from organ transplant rejection, xeno transplation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases in a mammal, including a human, comprising administering to said mammal an amount of an above described specifically preferred compound or a pharmaceutically acceptable salt thereof, effective in treating such a condition.

The present invention also relates to a compound of the formula

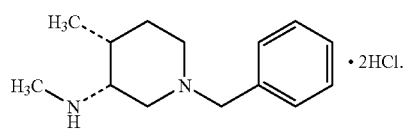

The present invention also relates to a compound of the formula

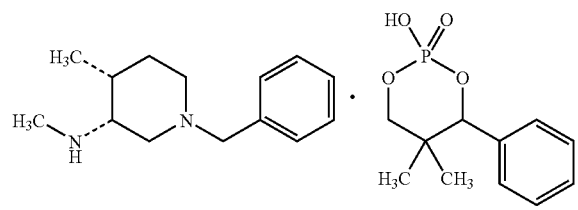

The present invention also relates to a compound of the formula

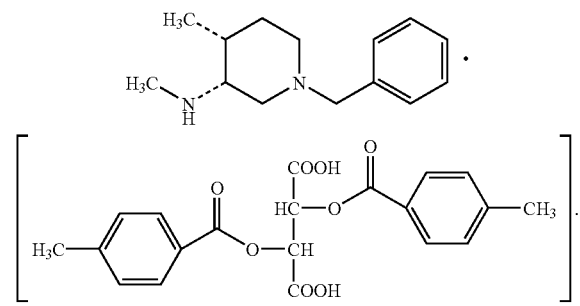

DETAILED DESCRIPTION OF THE INVENTION

The following reaction Schemes illustrate the preparation of the compounds of the present invention. Unless otherwise indicated R$^2$, R$^3$, R$^4$ and R$^5$ in the reaction Schemes and the discussion that follow are defined as above.

PREPARATION A
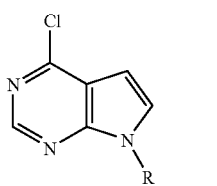
XXI
↓1
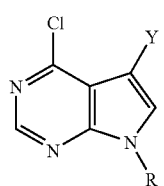
XX
↓2
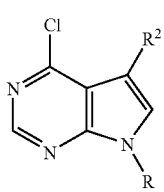
XIX
↓3
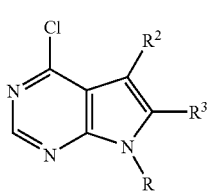
XVI
PREPARTION B
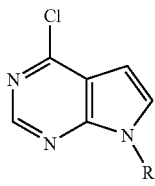
XXI
↓1
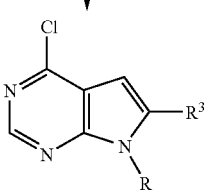
XXII
↓2
-continued
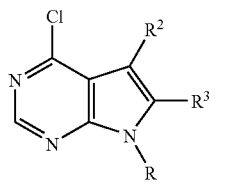
XVI
SCHEME 1
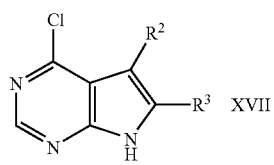
XVII
↓1
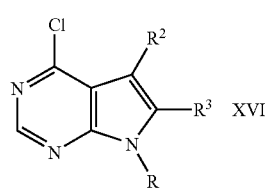
XVI
↓2
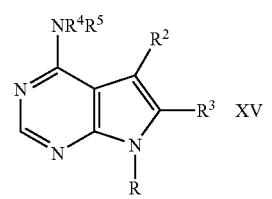
XV
↓3
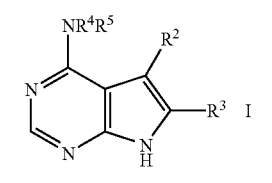
I
SCHEME 2
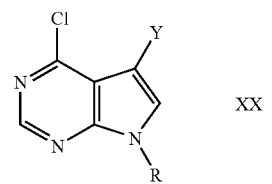
XX
↓1

-continued

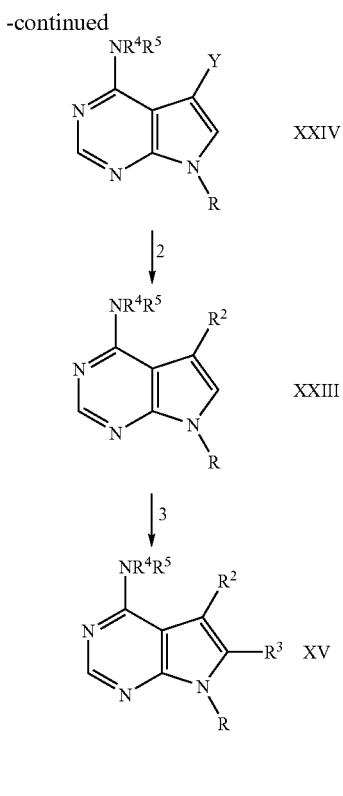

SCHEME 3

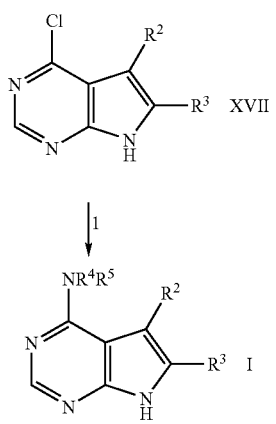

In reaction 1 of Preparation A, the 4-chloropyrrolo[2,3-d]pyrimidine compound of formula XXI, wherein R is hydrogen or a protecting group such as benzenesulfonyl or benzyl, is converted to the 4-chloro-5-halopyrrolo[2,3-d] pyrimidine compound of formula XX, wherein Y is chloro, bromo or iodo, by reacting XXI with N-chlorosuccinimide, N-bromosuccinimide or N-iodosuccinimide. The reaction mixture is heated to reflux, in chloroform, for a time period between about 1 hour to about 3 hours, preferably about 1 hour. Alternatively, in reaction 1 of Preparation A, the 4-chloropyrrolo[2,3-d]pyrimidine of formula XXI, wherein R is hydrogen, is converted to the corresponding 4-chloro-5-nitropyrrolo[2,3-d]pyrimidine of formula XX, wherein Y is nitro, by reacting XXI with nitric acid in sulfuric acid at a temperature between about −10° C. to about 10° C., preferably about 0° C., for a time period between about 5 minutes to about 15 minutes, preferably about 10 minutes. The compound of formula XXI, wherein Y is nitro, is converted to the corresponding 4-chloro-5-aminopyrrolo[2,3-d]pyrimidine of the formula XX, wherein Y is amino, by reacting XXI under a variety of conditions known to one skilled in the art such as palladium hydrogenolysis or tin(IV)chloride and hydrochloric acid.

In reaction 2 of Preparation A, the 4-chloro-5-halopyrrolo[2,3-d]pyrimidine compound of formula XX, wherein R is hydrogen, is converted to the corresponding compound of formula XIX, wherein $R^2$ is $(C_1-C_6)$alkyl or benzyl, by treating XX with N-butyllithium, at a temperature of about −78° C., and reacting the dianion intermediate so formed with an alkylhalide or benzylhalide at a temperature between about −78° C. to room temperature, preferably room temperature. Alternatively, the dianion so formed is reacted with molecular oxygen to form the corresponding 4-chloro-5-hydroxypyrrolo[2,3-d]pyrimidine compound of formula XIX, wherein $R^2$ is hydroxy. The compound of formula XX, wherein Y is bromine or iodine and R is benzenesulfonate, is converted to the compound of formula XIX, wherein $R^2$ is $(C_6-C_{12})$aryl or vinyl, by treating XX with N-butyllithium, at a temperature of about −78° C., followed by the addition of zinc chloride, at a temperature of about −78° C. The corresponding organo zinc intermediate so formed is then reacted with aryliodide or vinyl iodide in the presence of a catalytic quantity of palladium. The reaction mixture is stirred at a temperature between about 50° C. to about 80° C., preferably about 70° C., for a time period between about 1 hour to about 3 hours, preferably about 1 hour.

In reaction 3 of Preparation A, the compound of formula XIX is converted to the corresponding compound of formula XVI by treating XIX with N-butyllithium, lithium diisopropylamine or sodium hydride, at a temperature of about −78° C., in the presence of a polar aprotic solvent, such as tetrahydrofuran. The anionic intermediate so formed is further reacted with (a) alkylhalide or benzylhalide, at a temperature between about −78° C. to room temperature, preferably −78° C., when $R^3$ is alkyl or benzyl; (b) an aldehyde or ketone, at a temperature between about −78° C. to room temperature, preferably −78° C., when $R^3$ is alkoxy; and (c) zinc chloride, at a temperature between about −78° C. to room temperature, preferably −78° C., and the corresponding organozinc intermediate so formed is then reacted with aryliodide or vinyl iodide in the presence of a catalytic quantity of palladium. The resulting reaction mixture is stirred at a temperature between about 50° C. to about 80° C., preferably about 70° C., for a time period between about 1 hour to about 3 hours, preferably about 1 hour. Alternatively, the anion so formed is reacted with molecular oxygen to form the corresponding 4-chloro-6-hydroxypyrrolo[2,3-d]pyrimidine compound of formula XVI, wherein $R^3$ is hydroxy.

In reaction 1 of Preparation B, the 4-chloropyrrolo[2,3-d]pyrimidine compound of formula XXI is converted to the corresponding compound of formula XXII, according to the procedure described above in reaction 3 of Preparation A.

In reaction 2 of Preparation B, the compound of formula XXII is converted to the corresponding compound of formula XVI, according to the procedures described above in reactions 1 and 2 of Preparation A.

In reaction 1 of Scheme 1, the 4-chloropyrrolo[2,3-d]pyrimidine compound of formula XVII is converted to the corresponding compound of formula XVI, wherein R is benzenesulfonyl or benzyl, by treating XVII with benzenesulfonyl chloride, benzylchloride or benzylbromide in the presence of a base, such as sodium hydride or potassium carbonate, and a polar aprotic solvent, such as dimethylformamide or tetrahydrofuran. The reaction mixture is stirred at a temperature between about 0° C. to about 70° C., preferably about 30° C., for a time period between about 1 hour to about 3 hours, preferably about 2 hours.

In reaction 2 of Scheme 1, the 4-chloropyrrolo[2,3-d] pyrimidine compound of formula XVI is converted to the corresponding 4-aminopyrrolo[2,3-d]pyrimidine compound of formula XV by coupling XVI with an amine of the formula HNR⁴R⁵. The reaction is carried out in water or an alcohol solvent, such as tert-butanol, methanol or ethanol, or other high boiling organic solvents, such as dimethylformamide, triethylamine, 1,4-dioxane or 1,2-dichloroethane, at a temperature between about 60° C. to about 120° C., preferably about 80° C. Typical reaction times are between about 2 hours to about 100 hours, preferably about 48 hours. When $R^5$ is a nitrogen containing heterocycloalkyl group, each nitrogen must be protected by a protecting group, such a benzyl. Removal of the $R^5$ protecting group is carried out under conditions appropriate for that particular protecting group in use which will not affect the R protecting group on the pyrrolo[2,3-d] pyrimidine ring. Removal of the $R^5$ protecting group, when benzyl, is carried out in an alcohol solvent, such as ethanol, in the present of hydrogen and a catalyst, such as palladium hydroxide on carbon, at temperatures ranging from room temperature to about 70° C. The $R^5$ nitrogen containing hetrocycloalkyl group so formed may be further reacted with a variety of different electrophiles of formula II. For urea formation, electrophiles of formula II such as isocyanates, carbamates and carbamoyl chlorides are reacted with the $R^5$ nitrogen of the heteroalkyl group in a solvent, such as acetonitrile or dimethylformamide, in the presence of a base, such as sodium or potassium carbonate, at a temperature between about 20° C. to about 100° C. for a time period between about 24 hours to about 72 hours. For amide and sulfonamide formation, electrophiles of formula II, such as acylchlorides and sulfonyl chlorides, are reacted with the $R^5$ nitrogen of the heteroalkyl group in a solvent such as methylene chloride in the presence of a base such as pyridine at ambient temperatures for a time period between about 12 hours to about 24 hours. Amide formation may also be carried out by reacting a carboxylic acid with the heteroalkyl group in the presence of a carbodiimide such as 1-(3-dimethylaminopropyl)-3-ethylcarbodiimide in a solvent such as methylene chloride at ambient temperatures for about 12 to about 24 hours, or with an activated ester, such as N-hydroxysuccinimide ester, or 4-nitrophenyl ester in a solvent such as methylene chloride, tetrahydrofuran or ethanol. For alkyl formation, electrophiles of formula II, such as α,β-unsaturated amides, acids, nitriles, esters, and α-halo amides, are reacted with the $R^5$ nitrogen of the heteroalkyl group in a solvent such as methanol at ambient temperatures for a time period between about 12 hours to about 18 hours. Alkyl formation may also be carried out by reacting aldehydes with the heteroalkyl group in the presence of a reducing agent, such as sodium cyanoborohydride, in a solvent, such as methanol, at ambient temperature for a time period between about 12 hours to about 18 hours.

In reaction 3 of Scheme 1, removal of the protecting group from the compound of formula XV, wherein R is benzenesulfonyl, to give the corresponding compound of formula I, is carried out by treating XV with an alkali base, such as sodium hydroxide or potassium hydroxide, in an alcohol solvent, such as methanol or ethanol, or mixed solvents, such as alcohol/tetrahydrofuran or alcohol/water. The reaction is carried out at room temperature for a time period between about 15 minutes to about 1 hour, preferably 30 minutes. Removal of the protecting group from the compound of formula XV, wherein R is benzyl, is conducted by treating XV with sodium in ammonia at a temperature of about −78° C. for a time period between about 15 minutes to about 1 hour.

In reaction 1 of Scheme 2, the 4-chloropyrrolo[2,3-d] pyrimidine compound of formula XX is converted to the corresponding 4-aminopyrrolo[2,3-d]pyrimidine compound of formula XXIV, according to the procedure described above in reaction 2 of Scheme 1.

In reaction 2 of Scheme 2, the 4-amino-5-halopyrrolo[2,3-d]pyrimidine compound of formula XXIV, wherein R is benzenesulfonate and Z is bromine or iodine, is converted to the corresponding compound of formula XXIII by reacting XXIV with (a) arylboronic acid, when $R^2$ is aryl, in an aprotic solvent, such tetrahydrofuran or dioxane, in the presence of a catalytic quantity of palladium (0) at a temperature between about 50° C. to about 100° C., preferably about 70° C., for a time period between about 2 hours to about 48 hours, preferably about 12 hours; (b) alkynes, when $R^2$ is alkynyl, in the presence of a catalytic quantity of copper (I) iodide and palladium (0), and a polar solvent, such as dimethylformamide, at room temperature, for a time period between about 1 hour to about 5 hours, preferably about 3 hours; and (c) alkenes or styrenes, when $R^2$ is vinyl or styrenyl, in the presence of a catalytic quantity of palladium in dimethylformamide, dioxane or tetrahydrofuran, at a temperature between about 80° C. to about 100° C., preferably about 100° C., for a time period between about 2 hours to about 48 hours, preferably about 48 hours.

In reaction 3 of Scheme 2, the compound of formula XXIII is converted to the corresponding compound of formula XV, according to the procedure described above in reaction 3 of Preparation A.

In reaction 1 of Scheme 3, the compound of formula XVII is converted to the corresponding compound of formula I, according to the procedure described above in reaction 2 of Scheme 1.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as acetone, methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the calcium, sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compositions of the present invention may be formulated in a conventional manner using one or more pharmaceutically acceptable carriers. Thus, the active compounds of the invention may be formulated for oral, buccal, intranasal, parenteral intravenous, (e.g., intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Attentively, the active ingredient may be in powder form for reconstitution with a suitable vehicle, e.g., sterile pyrogen-free water, before use. The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., rheumatoid arthritis) is 0.1 to 1000 mg of the active ingredient per unit dose which could be administered, for example, 1 to 4 times per day.

Aerosol formulations for treatment of the conditions referred to above (e.g., asthma) in the average adult human are preferably arranged so that each metered dose or "puff" of aerosol contains 20 µg to 1000 µg of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

A compound of formula (I) administered in a pharmaceutically acceptable form either alone or in combination with one or more additional agents which modulate a mammlian immune system or with antiinflammatory agents, agents which may include but are not limited to cyclosporin A (e.g. Sandimmune® or Neoral®, rapamycin, FK-506 (tacrolimus), leflunomide, deoxyspergualin, mycophenolate (e.g. Cellcept®, azathioprine (e.g. Imuran®)), daclizumab (e.g. Zenapax®), OKT3 (e.g. Orthocolone®), AtGam, aspirin, acctaminophen, ibuprofen, naproxen, piroxicam, and antiinflammatory steroids (e.g. prednisolone or dexamethasone); and such agents may be administered as part of the same or separate dosage forms, via the same or different routes of administration, and on the same or different administration schedules according to standard pharmaceutical practice.

FK506 (Tacrolimus) is given orally at 0.10–0.15 mg/kg body weight, every 12 hours, within first 48 hours postoperative. Does is monitored by serum Tacrolimus trough levels.

Cyclosporin A (Sandimmune oral or intravenous formulation, or Neoral®, oral solution or capsules) is given orally at 5 mg/kg body weight, every 12 hours within 48 hours postoperative. Dose is monitored by blood Cyclosporin A trough levels.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The ability of the compounds of formula I or their pharmaceutically acceptable salts to inhibit Janus Kinase 3 and, consequently, demonstrate their effectiveness for treating disorders or conditions characterized by Janus Kinase 3 is shown by the following in vitro assay tests.

Biological Assay

JAK3 (JH1:GST) Enzymatic Assay

The JAK3 kinase assay utilizes a protein expressed in baculovirus-infected SF9 cells (a fusion protein of GST and the catalytic domain of human JAK3) purified by affinity chromatography on glutathione-Sepaharose. The substrate for the reaction is poly-Glutamic acid-Tyrosine (PGT (4:1), Sigma catalog #P0275), coated onto Nunc Maxi Sorp plates at 100 µg/ml overnight at 37° C. The morning after coating, the plates are washed three times and JAK3 is added to the wells containing 100 µl of kinase buffer (50 mM HEPES, pH 7.3, 125 mM NaCl, 24 mM MgCl2)+0.2 uM ATP+1 mM Na orthovanadate.) The reaction proceeds for 30 minutes at room temperature and the plates is washed three more times. The level of phosphorylated tyrosine in a given well is quantitated by standard ELISA assay utilizing an anti-phosphotyrosine antibody (ICN PY20, cat. #69-151-1).

Inhibition of Human IL-2 Dependent T-Cell Blast Proliferation

This screen measures the inhibitory effect of compounds on IL-2 dependent T-Cell blast proliferation in vitro. Since signaling through the IL-2 receptor requires JAK-3, cell active inhibitors of JAK-3 should inhibit IL-2 dependent T-Cell blast proliferation.

The cells for this assay are isolated from fresh human blood. After separation of the mononuclear cells using Accuspin System-Histopaque-1077 (Sigma #A7054), primary human T-Cells are isolated by negative selection using Lympho-Kwik T (One Lambda, Inc., Cat #LK-50T). T-Cells are cultured at $1-2 \times 10^6$/ml in Media (RPMI+10% heat-inactivated fetal calf serum (Hyclone Cat #A-1111-L)+1% Penicillin/Streptomycin (Gibco)) and induce to proliferate by the addition of 10 ug/ml PHA (Murex Diagnostics, Cat #HA 16). After 3 days at 37° C. in 5% $CO_2$, cells are washed 3 times in Media, resuspended to a density of $1-2 \times 10^6$ cells/ml in Media plus 100 Units/ml of human recombinant IL-2 (R&D Systems, Cat #202-IL). After 1 week the cells are IL-2 dependent and can be maintained for up to 3 weeks by feeding twice weekly with equal volumes of Media+100 Units/ml of IL-2.

To assay for a test compounds ability to inhibit IL-2 dependent T-Cell proliferation, IL-2 dependent cells are washed 3 times, resuspended in media and then plated (50,000 cells/well/0.1 ml) in a Flat-bottom 96-well microtiter plate (Falcon #353075). From a 10 mM stock of test compound in DMSO, serial 2-fold dilutions of compound are added in triplicate wells starting at 10 uM. After one hour, 10 Units/ml of IL-2 is added to each test well. Plates are then incubated at 37° C., 5% $CO_2$ for 72 hours. Plates are then pulsed with $^3$H-thymidine (0.5 uCi/well) (NEN Cat #NET-027A), and incubated an additional 18 hours. Culture plates are then harvested with a 96-well plate harvester and the amount of $^3$H-thymidine incorporated into proliferating cells is determined by counting on a Packard Top Count scintillation counter. Data is analyzed by plotting the % inhibition of proliferation verses the concentration of test compound. An $IC_{50}$ value (uM) is determined from this plot.

The following Examples illustrate the preparation of the compounds of the present invention but it is not limited to the details thereof. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20–25° C.

EXAMPLE 1 (Stable Salt Formation)

(1-benzyl-4-methylpiperidin-3-yl)-methylamine bishydrochloride

To a solution of 23.4 kg of (1-benzyl-4-methylpiperidin-3-yl)-methylamine in 10 liters of toluene and 120 liters of ethanol at 3° C. was added 25 liters of 32% HCl in water, keeping the reaction temperature below 10° C. 100 liters of solvent was distilled off under partial vacuum, and 215 liters of ethyl acetate was added at 30° C. 210 liters of solvent was distilled off under partial vacuum, and a second 215 liters of ethyl acetate was added and another 210 liters of solvent was distilled off under partial vacuum. 111 liters of acetone was added at 35 C.°, the suspension was cooled to 0° C., and then the product, (1-benzyl-4-methylpiperidin-3-yl)-methylamine bishydrochloride, was filtered off and washed with 55 liters of acetone. The wet-cake was reslurried 3 times in ethanol (10 volume equivalents at reflux) to upgrade the diasteromeric ratio of cis:trans from 91:9 to greater than 97:3. Total recovery was 19.4 kg, 62% yield. 1H NMR ($CD_3OD$, 400 MHz): 7.55 (m, 5H), 4.88 (s, 3H), 4.52 (d, J=12.8 Hz, 1H), 4.45 (d, J=12.8 Hz, 1H), 3.76 (m, 1H), 3.67 (m, 1H), 3.40–3.00 (m, 3H), 2.78 (3, 3H), 2.55 (m, 1H), 2.14 (m, 1H), 1.90 (m, 1H), 1.16 (d, J=7.2 Hz, 3H)

EXAMPLE 2 (Resolution)

bis[(1-benzyl-4-methylpiperidin-3-yl)-methylamine] di-p-toluyl-L-tartrate

To a solution of 9.5 kg of (1-benzyl-4-methylpiperidin-3-yl)-methylamine bishydrochloride in 16 liters of water was added 33 liters of 2N sodium hydroxide. Solids precipitated from the mixture. The slurry was diluted with 43 liters of isopropanol and 11 liters of methanol to redissolve the solids. Di-p-toluyl-L-tartaric acid (6.3 kg) was added, with precipitation of solids. The slurry was heated to reflux to redissolve the solids, then slowly cooled to 72° C. Seeds of bis[(1-benzyl-4-methylpiperidin-3-yl)-methylamine]di-p-toluyl-L-tartrate were added (180 grams), and the hazy solution was slowly cooled to 15° C. The solids were filtered and washed with isopropanol to yield 5.9 kg of bis[(1-benzyl-4-methylpiperidin-3-yl)-methylamine]di-p-toluyl-L-tartrate in 44% yield. 1H NMR ($CD_3OD$, 400 MHz): 8.04 (d, J=8.4 Hz, 2H), 7.30 (m, 7H), 5.86 (s, 1H), 4.91 (s, 3H), 3.64 (d, J=12.8 Hz, 1H), 3.41 (d, J=12.8 Hz, 1H), 3.09 (s, 1H), 2.90 (m, 2H), 2.40 (s, 3H), 2.22 (m, 2H), 1.92 (m, 1H), 1.57 (m, 2H), 1.03 (d, J=7.2 Hz, 3H)

EXAMPLE 3 (Phencyphos Resolution)

To a solution of 6.83 grams (31.3 mmol) in 250 ml IPA and 10 ml water was added 7.57 g (+) phencyphos (31.3 mmol), and the mixture was heated to reflux in order to obtain a clear solution. At a temperature of approximately 65° C. seeding crystals with an ee of 90% were added. Crystallization started within one hour and the mixture was allowed to reach room temperature overnight. Isolation afforded 6.85 g (47%) with an ee of 99%. The filtrate was concentrated, TBME, water and $K_2CO_3$ were added, and the layers separated. The organic layer was dried ($Na_2SO_4$)) and the solvent evaporated. The resulting oil (3.99 grams) was dissolved in 200 ml IPA and 10 ml water and 4.4 grams(−) phencyphos was added. The mixture was heated to reflux and allowed to cool to room temperature overnight. This afforded 6 grams (41%) salt with an ee of 99.9+% Analyses were performed on the free amine. The free amine was obtained by treatment of the salt with TBME, water and $K_2CO_3$.

The following schematically illustrate the methods of Examples 1 to 3 (wherein Bn is defined as benzyl (—$CH_2$—$C_6H_5$)):

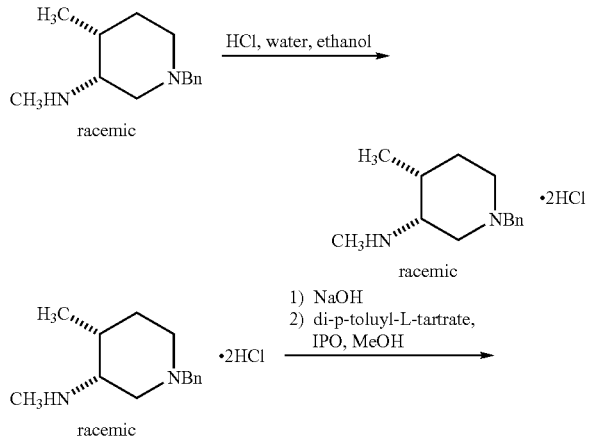

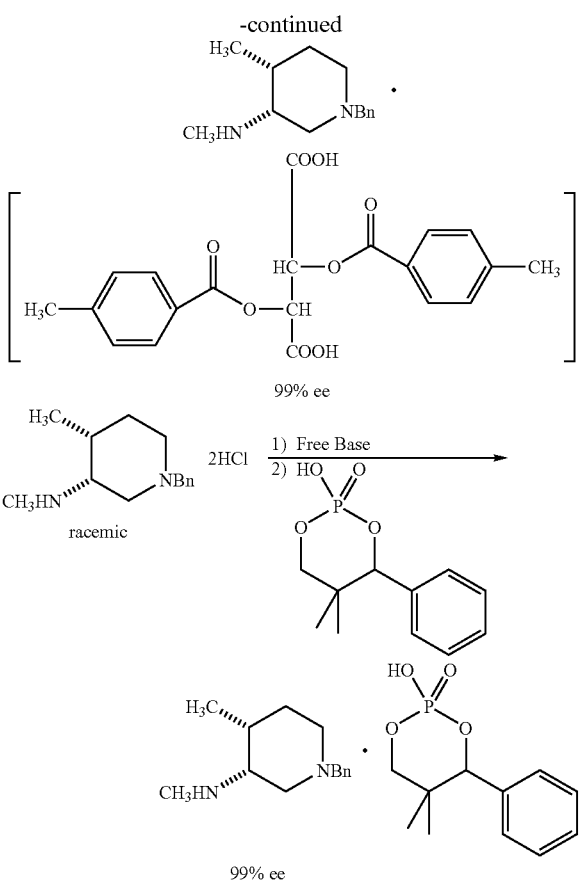

99% ee

EXAMPLE 4

A racemic mixture of the compound of formula III was resolved:

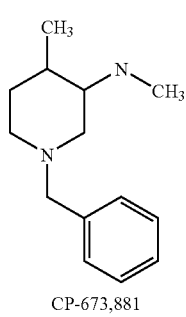

CP-673,881

Sample Processing

A compound of formula III was filtered through a 0.2 um nylon 66 filter disc.

Procedure: (96% Ethanol 4% Water as Solvent)

0.8711 grams of the compound of formula III, of the filtrate, was dissolved in 5.0 ml of a 96:4 ratio of ethanol/water. 1.544 grams of di-p-toluoyl-L-tartaric acid was added and the mixture was stirred to obtain a clear solution. The solution was allowed to stand at room temperature for approximately 4 hours. The resulting slurry was filtered onto Whatman #2 filter paper and washed with 4.0 ml of a 96:4 ratio of ethanol/water. The solids were air dried to give 0.488 grams of the diastereomer salt.

0.488 grams of the diastereomer salt was suspended in 50 ml of water then 50 ml of methylene chloride was added. The pH of the mixture was adjusted to approximately 9 using saturated sodium bicarbonate followed by 1.0N sodium hydroxide. Upon completion of the pH adjustment, the layers were separated and the methylene chloride layer was filtered through Whatman #2 filter paper. Solvents were then removed by reduced pressure evaporation to give a light orange colored oil. Weight not determined. This oil was evaluated by gas chromatography.

Analytical assay: 97.3% desired enantiomer by normalized area percent.

EXAMPLE 5

Procedure: (100% Ethanol as Solvent)

0.8714 grams of (1-benzyl-4-methyl-piperidin-3-yl)-methyl-amine was dissolved in 5.0 ml of 200 proof ethanol. 1.544 grams of di-p-toluoyl-L-tartaric acid was added and the mixture was stirred to obtain a clear solution. The solution was allowed to stand at room temperature for approximately 4 hours. The resulting slurry was filtered onto Whatman #2 filter paper and washed with 4.0 ml of a 96:4 ratio of ethanol/water. The solids were air dried to give 0.628 grams of the diastereomer salt.

0.628 grams of the diastereomer salt was suspended in 50 ml of water then 50 ml of methylene chloride was added. The pH of the mixture was adjusted to approximately 9 using saturated sodium bicarbonate followed by 0.1N sodium hydroxide. Upon completion of the pH adjustment, the layers were separated and the methylene chloride layer was filtered through Whatman #2 filter paper. Solvents were then removed by reduced pressure evaporation to give a light yellow colored oil. Weight not determined. Evaluation of the oil provided the analytical assay: 90.5% desired enantiomer by normalized area percent.

EXAMPLE 6

3-{(3R,4R)-4-Methyl-3-[methyl-(7H-pyrrolo[2,3-d]pyrimidin-4-yl)-amino]-piperidin-1-yl}-3-oxo-propionitrile Method A (3R,4R)-(1-Benzyl-4-methyl-piperidin-3-yl)-methyl-(7H-pyrrolo[2,3-d]pyrimidin-4-yl)-amine 4-Chloropyrrolo[2,3-d]pyrimidine (5.37 grams, 34.9 mmol), prepared by the method of Davoll, J. Am. Chem. Soc., 82, 131 (1960), which is incorporated by reference in its entirety, the product from Example 2 (6 grams, 27.5 mmol) and potassium carbonate (11.4 grams, 82.5 mmol) were combined in water (60 ml). The slurry was heated at reflux for 90 hrs. The mixture was cooled to 90° C. and toluene (60 ml) was added. The biphasic mixture was filtered through filter aid and the layers were separated. The aqueous layer was extracted with toluene. The combined toluene layers were washed with 1N NaOH, treated with activated charcoal, and filtered through filter aid. The toluene was evaporated in vacuo and the residue crystallized from a 1:1 mixture of isopropyl acetate and hexanes to afford 5 grams of an off-white solid; 54% yield. LRMS: 336.1 (M+1).

Method B

Methyl-((3R,4R)-4-methyl-piperidin-3-yl)-(7H-pyrrolo[2,3-d]pyrimidin-4-yl)-amine To the product from Method A (0.7 grams, 2.19 mmol) dissolved in 15 mL of ethanol was added 1.5 mL of 2 N hydrochloric acid and the reaction mixture degassed by nitrogen purge. To the reaction mixture was then added 0.5 grams of 20% palladium hydroxide on carbon (50% water) (Aldrich) and the resulting mixture shaken (Parr-Shaker) under a 50 psi atmosphere of hydrogen at room temperature for 2 days. The Celite filtered reaction mixture was concentrated to dryness in vacuo and the residue purified by flash chromatography (silica; 5% methanol in dichoromethane) affording 0.48 grams (90%) of the title compound. LRMS: 246.1 (M+1).

Method C

3-{(3R,4R)-4-Methyl-3-[methyl-(7H-pyrrolo[2,3-d]pyrimidin4-yl)-amino]-piperidin-1-yl}-3-oxo-propionitrile To a stirred solution of the product from Method B (1.0 g) dissolved in 30 mL of ethanol was added 0.82 g of cyanoacetic acid 2,5-dioxo-pyrrolidin-1-yl ester and the resulting mixture stirred at room temperature for 2 h. The reaction mixture was filtered through Celite® and concentrated in vacuo. The residue was redissolved in dichloromethane, washed with saturated, aqueous sodium bicarbonate, dried over sodium sulfate, filtered and concentrated to dryness in vacuo affording 1.1 g (86%) of the title compound as a yellow foam. LRMS: 313 (M+1).

EXAMPLE 7

1-{(3R,4R)-4-Methyl-3-[methyl-(7H-pyrrolo[2,3-d]pyrimidin-4-yl)-amino]-piperidin-1-yl}-ethanone To a stirred solution of the product from Method B (0.03 grams, 0.114 mmol) dissolved in 5 mL of 10:1 dichloromethane/pyridine was added (0.018 grams, 0.228 mmol) of acetylchloride and the resulting mixture stirred at room temperature for 18 hours. The reaction mixture was then partitioned between dichloromethane and saturated sodium bicarbonate (NaHCO₃). The organic layer was washed again with saturated NaHCO₃, dried over sodium sulfate and concentrated to dryness in vacuo. The residue was purified by preparative thin layer chromatography (PTLC) (silica; 4% methanol in dichloromethane) affording 0.005 g (15%) of the title compound as a colorless oil.

The title compounds for examples 8–31 were prepared by a method analogous to that described in Example 7.

EXAMPLE 8

(3R,4R)-[1-(2-Amino-ethanesulfonyl)-4-methyl-piperidin-3-yl-methyl-(7H-pyrrolo[2,3-d]pyrimidin-4-yl)-amine

EXAMPLE 9

(3R,4R)-(1-Ethanesulfonyl-4-methyl-piperidin-3-yl)-methyl-(7H-pyrrolo[2,3-d]pyrimidin-4-yl)-amine

EXAMPLE 10

(3R,4R)-[1-(Butane-1-sulfonyl)-4-methyl-piperidin-3-yl-methyl-(7H-pyrrolo[2,3-d]pyrimidin-4-yl)-amine

EXAMPLE 11

(3R,4R)-4-Methyl-3-[methyl-(7H-pyrrolo[2,3-d]pyrimidin-4-yl)-amino]-piperidine-1-carboxylic acid isobutyl ester

EXAMPLE 12

N-(2-{(3R,4R)-4-Methyl-3-[methyl-(7H-pyrrolo[2,3-d]pyrimidin-4-yl)-amino]-piperidine-1-sulfonyl}-ethyl)-propionamide

EXAMPLE 13

(2-{(3R,4R)-4-Methyl-3-[methyl-(7H-pyrrolo[2,3-d]pyrimidin4-yl)-amino]-piperidine-1-sulfonyl}-ethyl)-carbamic acid methyl ester

EXAMPLE 14

N-(2-{(3R,4R)-4-Methyl-3-[methyl-(7H-pyrrolo[2,3-d]pyrimidin-4-yl)-amino]-piperidine-1-sulfonyl}-ethyl)-isobutyramide

EXAMPLE 15

(3R,4R)-(1-Methanesulfonyl-piperidin-3-yl)-methyl-(7H-pyrrolo[2,3-d]pyrimidin-4-yl)-amine

EXAMPLE 16

((3R,4R)-1-Ethanesulfonyl-piperidin-3-yl)-methyl-(7H-pyrrolo[2,3-d]pyrimidin-4-yl)-amine

EXAMPLE 17

(3R,4R)-Methyl-[1-(propane-1-sulfonyl)-piperidin-3-yl-(7H-pyrrolo[2,3-d]pyrimidin-4-yl)-amine

EXAMPLE 18

(3R,4R)-]1-(Butane-1-sulfonyl)-piperidin-3-yl-methyl-(7H-pyrrolo[2,3-d]pyrimidin-4-yl)-amine

EXAMPLE 19

2,2-Dimethyl-N-((3R,4R)-2-{4-methyl-3-]methyl-(7H-pyrrolo[2,3-d]pyrimidin-4-yl)-amino]-piperidine-1-sulfonyl-ethyl)-propionamide

EXAMPLE 20

(3-{(3R,4R)-4-Methyl-3-[methyl-(7H-pyrrolo[2,3-d]pyrimidin-4-yl)-amino]-piperidin-1-yl}-3-oxo-propyl)-carbamic acid tert-butyl ester

EXAMPLE 21

Methyl-[(3R,4R)-4-methyl-1-(propane-1-sulfonyl)-piperidin-3-yl]-(7H-Pyrrolo[2,3-d]pyrimidin-4-yl)-amine

EXAMPLE 22

3-Amino-1-{(3R,4R)-4-methyl-3-[methyl-(7H-pyrrolo[2,3-d]pyrimidin-4-yl)-amino]-piperidin-1-yl}-propan-1-one

EXAMPLE 23

2-Methoxy-1-{(3R,4R)-4-methyl-3-[methyl-(7H-pyrrolo[2,3-d]pyrimidin-4-yl)-amino]-piperidin-1-yl}-ethanone

EXAMPLE 24

2-Dimethylamino-1-[(3R,4R)-4-methyl-3-[methyl-(7H-pyrrolo[2,3-d]pyrimidin-4-yl)-amino]-piperidin-1-yl}-ethanone

EXAMPLE 25

(3-{(3R,4R)-4-Methyl-3-[methyl-(7H-pyrrolo[2,3-d]pyrimidin-4-yl)-amino]-piperidin-yl}-3-oxo-propyl)-carbamic acid tert-butyl ester

EXAMPLE 26

3,3,3-Trifluoro-1-{(3R,4R)-4-methyl-3-[methyl-(7H-pyrrolo[2,3-d]pyrimidin-4-yl)-amino]-piperidin-1-yl}-propan-1-one

EXAMPLE 27

N-(2-{(3R,4R)-4-Methyl-3-[methyl-(7H-pyrrolo[2,3-d]pyrimidin-4-yl)-amino]-piperidin-1-yl}-2-oxo-ethyl)-acetamide

EXAMPLE 28

3-Ethoxy-1-{(3R,4R)-4-methyl-3-[methyl-(7H-pyrrolo[2,3-d]pyrimidin-4-yl)-amino]-piperidin-1-yl}-propan-1-one

EXAMPLE 29

(3R,4R)-4-Methyl-3-[methyl-(7H-pyrrolo[2,3-d]pyrimidin-4-yl)-amino]-piperidine-1-carboxylic acid methylamide

EXAMPLE 30

(3R,4R)-4-Methyl-3-[methyl-(7H-pyrrolo[2,3-d]pyrimidin-4-yl)-amino]-piperidine-1-carboxylic acid diethylamide

EXAMPLE 31

(3R,4R)-Methyl-[4-methyl-1-(2-methylamino-ethanesulfonyl)-piperidin-3-yl]-(7H-pyrrolo[2,3-d]pyrimidin-4-yl)-amine

What is claimed is:

1. A method for resolving enantiomers of a compound containing the structure of the formula:

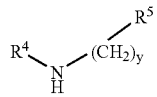

pharmaceutically acceptable acid addition salts thereof, pharmaceutically acceptable base addition salts thereof and free base thereof;

wherein y is 0, 1 or 2;

$R^4$ is selected from the group consisting of hydrogen, $(C_1-C_6)$alkyl, $(C_1-C_6)$alkylsulfonyl, $(C_2-C_6)$alkenyl, $(C_2-C_6)$alkynyl wherein the alkyl, alkenyl and alkynyl groups are optionally substituted by deuterium, hydroxy, amino, trifluoromethyl, $(C_1-C_4)$alkoxy, $(C_1-C_6)$acyloxy, $(C_1-C_6)$alkylamino, $((C_1-C_6)$alkyl$)_2$amino, cyano, nitro, $(C_2-C_6)$alkenyl, $(C_2-C_6)$alkynyl or $(C_1-C_6)$acylamino; or $R^4$ is $(C_3-C_{10})$cycloalkyl wherein the cycloalkyl group is optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano $(C_1-C_6)$alkyl, trifluoromethyl$(C_1-C_6)$alkyl, nitro, nitro $(C_1-C_6)$alkyl or $(C_1-C_6)$acylamino;

$R^5$ is $(C_1-C_9)$heterocycloalkyl wherein the heterocycloalkyl groups must be substituted by one to five carboxy, cyano, amino, deuterium, hydroxy, $(C_1-C_6)$alkyl, $(C_1-C_6)$alkoxy, halo, $(C_1-C_6)$acyl, $(C_1-C_6)$alkylamino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, amino$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_5)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_6)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl; or a group of the formula

II

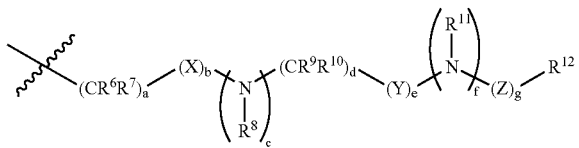

wherein a is 0, 1, 2, 3 or 4;

b, c, e, f and g are each independently 0 or 1;

d is 0, 1, 2, or 3;

X is $S(O)_n$ wherein n is 0, 1 or 2; oxygen, carbonyl or —C(=N-cyano)-;

Y is $S(O)_n$ wherein n is 0, 1 or 2; or carbonyl; and

Z is carbonyl, C(O)O—, C(O)NR— or $S(O)_n$ wherein n is 0, 1 or 2;

$R^6$, $R^7$, $R^8$, $R^9$, $R^{10}$ and $R^{11}$ are each independently selected from the group consisting of hydrogen or $(C_1-C_6)$alkyl optionally substituted by deuterium, hydroxy, amino, trifluoromethyl, $(C_1-C_6)$acyloxy, $(C_1-C_6)$acylamino, $(C_1-C_6)$alkylamino, $((C_1-C_6)$alkyl$)_2$amino, cyano, cyano$(C_1-C_6)$alkyl, trifluoromethyl$(C_1-C_6)$alkyl, nitro, nitro$(C_1-C_6)$alkyl or $(C_1-C_6)$acylamino;

$R^{12}$ is carboxy, cyano, amino, oxo, deuterium, hydroxy, trifluoromethyl, $(C_1-C_6)$alkyl, trifluoromethyl$(C_1-C_6)$alkyl, $(C_1-C_6)$alkoxy, halo, $(C_1-C_6)$acyl, $(C_1-C_6)$alkylamino, $((C_1-C_6)$alkyl$)_2$amino, amino$(C_1-C_6)$alkyl, $(C_1-C_6)$alkoxy-CO—NH, $(C_1-C_6)$alkylamino-CO—, $(C_2-C_6)$alkenyl, $(C_2-C_6)$alkynyl, $(C_1-C_6)$alkylamino, hydroxy$(C_1-C_6)$alkyl, $(C_1-C_6)$alkoxy$(C_1-C_6)$alkyl, $(C_1-C_6)$acyloxy$(C_1-C_6)$alkyl, nitro, cyano$(C_1-C_6)$alkyl, halo$(C_1-C_6)$alkyl, nitro$(C_1-C_6)$alkyl, trifluoromethyl, trifluoromethyl$(C_1-C_6)$alkyl, $(C_1-C_6)$acylamino, $(C_1-C_6)$acylamino$(C_1-C_6)$alkyl, $(C_1-C_8)$alkoxy$(C_1-C_6)$acylamino, amino$(C_1-C_6)$acyl, amino$(C_1-C_6)$acyl$(C_1-C_6)$alkyl, $(C_1-C_6)$alkylamino$(C_1-C_6)$acyl, $((C_1-C_6)$alkyl$)_2$amino$(C_1-C_6)$acyl, $R^{15}R^{16}N$—CO—O—, $R^{15}R^{16}N$—CO—$(C_1-C_6)$alkyl, $R^{15}C(O)NH$, $R^{15}OC(O)NH$, $R^{15}NHC(O)NH$, $(C_1-C_6)$alkyl-$S(O)_m$, $(C_1-C_6)$alkyl-$S(O)_m$—$(C_1-C_6)$alkyl, $R^{15}R^{16}NS(O)_m$, $R^{15}R^{16}NS(O)_m(C_1-C_6)$alkyl, $R^{15}S(O)_mR^{16}N$, $R^{15}S(O)_mR^{16}N(C_1-C_6)$alkyl wherein m is 0, 1 or 2 and $R^{15}$ and $R^{16}$ are each independently selected from hydrogen or $(C_1-C_6)$alkyl;

said method comprising the steps of:

a) mixing a racemic mixture of enantiomers of a compound, cantaining the structure of said formula; in a solvent, with a resolving compound having a defined stereospecificity, to orm a solution and with said resolving agent being capable of binding with at least one but not all of said enantiomers to form a precipitate, containing said at least one of said enantiomers, b) allowing the mixture to stand for a time sufficient to allow substantial precipitation of a stereospecific enantiomer of the racemic mixture from the solution and wherein another of said enantiomers remains in said solution; and c) depending on the stereospecific enantiomer of the compound which is desired, collecting either the precipitate and purifying it or collecting the solution with contained other of said enantiomers and recrystallizing the enantiomer contained in said solution.

* * * * *

UNITED STATES PATENT AND TRADEMARK OFFICE
CERTIFICATE OF CORRECTION

| | | |
|---|---|---|
| PATENT NO. | : 7,301,023 B2 | Page 1 of 1 |
| APPLICATION NO. | : 10/154699 | |
| DATED | : November 27, 2007 | |
| INVENTOR(S) | : Mark E. Flanagan et al. | |

It is certified that error appears in the above-identified patent and that said Letters Patent is hereby corrected as shown below:

Delete COLUMN 27 and COLUMN 28

COLUMN 27
Lines 1 - 4, should read as follows:

What is claimed is:
1. The compound 3-{(3R,4R)-4-Methyl-3-[methyl-(7H-pyrrolo[2,3-d]pyrimidin-4-yl)-amino]-piperidin-1-yl}-3-oxo-propionitrile or a pharmaceutically acceptable salt thereof.

Signed and Sealed this

Seventeenth Day of February, 2009

JOHN DOLL
*Acting Director of the United States Patent and Trademark Office*

Disclaimer

7,301,023 B2 — Mark E. Flanagan, Gales Ferry, CT (US); Michael J. Munchhof, Salem, CT (US). CHIRAL SALT RESOLUTION. Patent dated November 27, 2007. Disclaimer filed July 26, 2019, by the assignee, Pfizer, Inc.

Hereby disclaim the term of this patent which would extend beyond Patent No. RE41,783.

*(Official Gazette, April 7, 2020)*